(12) United States Patent
Yu et al.

(10) Patent No.: US 9,696,283 B1
(45) Date of Patent: Jul. 4, 2017

(54) APPARATUS AND METHODS FOR PHOTOACOUSTIC MEASUREMENT OF LIGHT ABSORPTION OF PARTICULATE AND GASEOUS SPECIES

(71) Applicant: Aerodyne Research, Inc., Billerica, MA (US)

(72) Inventors: Zhenhong Yu, Arlington, MA (US);
Paul L. Kebabian, Billerica, MA (US);
William Brown, Billerica, MA (US);
James Assif, Billerica, MA (US)

(73) Assignee: Aerodyne Research, Inc., Billerica, MA (US)

( * ) Notice: Subject to any disclaimer, the term of this patent is extended or adjusted under 35 U.S.C. 154(b) by 0 days.

(21) Appl. No.: 15/290,706

(22) Filed: Oct. 11, 2016

(51) Int. Cl.
*G01N 21/00* (2006.01)
*G01N 29/24* (2006.01)
*G01N 29/02* (2006.01)

(52) U.S. Cl.
CPC ......... *G01N 29/2418* (2013.01); *G01N 29/02* (2013.01); *G01N 2291/021* (2013.01); *G01N 2291/103* (2013.01)

(58) Field of Classification Search
USPC .......................... 73/24.02, 28.02, 31.05, 23.2
See application file for complete search history.

(56) References Cited

U.S. PATENT DOCUMENTS

| | | | |
|---|---|---|---|
| 4,187,026 A | 2/1980 | Schaffer et al. | |
| 6,067,840 A * | 5/2000 | Chelvayohan | G01N 21/3504 250/343 |
| 6,662,627 B2 | 12/2003 | Arnott et al. | |
| 6,672,135 B2 * | 1/2004 | Adiletta | B01D 46/543 210/321.84 |
| 7,170,607 B2 * | 1/2007 | Yoon | G01N 21/1702 356/432 |
| 7,301,639 B1 | 11/2007 | Kebabian et al. | |
| 7,304,732 B1 | 12/2007 | Polcawich et al. | |
| 7,398,672 B2 | 7/2008 | Riddle | |

(Continued)

OTHER PUBLICATIONS

Amaral, Simone Simoes, et al., "An Overview of Particulate Matter Measurement Instruments," Atmosphere, vol. 6, Sep. 9, 2015, pp. 1327-1345.

(Continued)

*Primary Examiner* — Jewel V Thompson
(74) *Attorney, Agent, or Firm* — Cesari and McKenna, LLP; James A. Blanchette (57) ABSTRACT

In one embodiment, a photoacoustic effect measurement instrument for measuring a species (e.g., a species of PM) in a gas employs a pair of differential acoustic cells including a sample cell that receives sample gas including the species, and a reference cell that receives a filtered version of the sample gas from which the species has been substantially removed. An excitation light source provides an amplitude modulated beam to each of the acoustic cells. An array of multiple microphones is mounted to each of the differential acoustic cells, and measures an acoustic wave generated in the respective acoustic cell by absorption of light by sample gas therein to produce a respective signal. The microphones are isolated from sample gas internal to the acoustic cell by a film. A preamplifier determines a differential signal and a controller calculates concentration of the species based on the differential signal.

30 Claims, 3 Drawing Sheets

(56) References Cited

U.S. PATENT DOCUMENTS

| | | | |
|---|---|---|---|
| 7,710,566 B2 | 5/2010 | Arnott et al. | |
| 8,115,931 B2 | 2/2012 | Miklos et al. | |
| 8,364,430 B2 | 1/2013 | Kebabian | |
| 8,701,465 B2 | 4/2014 | Shubinsky et al. | |
| 2005/0121614 A1* | 6/2005 | Stuttard | G01N 21/3504 250/343 |
| 2008/0257016 A1* | 10/2008 | Fujii | G01N 27/4062 73/31.05 |
| 2009/0320561 A1* | 12/2009 | Fritz | B82Y 20/00 73/24.02 |
| 2010/0018288 A1* | 1/2010 | Yamanaka | G01N 29/022 73/24.02 |
| 2013/0008230 A1* | 1/2013 | Avramescu | G01N 21/1702 73/24.02 |

OTHER PUBLICATIONS

Arnott, W. Patrick, et al., "Photoacoustic Spectrometer for Measuring Light Absorption by Aerosol: Instrument Description," Elsevier Science Ltd., Pergamon, Atmospheric Environment, vol. 33, Issue 17, Aug. 1999, pp. 2845-2852.

Miklos, Andras, et al., "Photoacoustic Spectroscopy, Theory," Academic Press, Dec. 1999, pp. 1815-1822.

* cited by examiner

APPARATUS AND METHODS FOR PHOTOACOUSTIC MEASUREMENT OF LIGHT ABSORPTION OF PARTICULATE AND GASEOUS SPECIES

STATEMENT REGARDING FEDERALLY SUPPORTED RESEARCH

This invention was made with Government support under National Aeronautics and Space Administration (NASA) Small Business Innovation Research (SBIR) contract Nos. NNX13CL42P and NNX14CL90C. The Government has certain rights in this invention.

BACKGROUND

Technical Field

The present disclosure relates generally to measuring a species in a gas, and more specifically to methods and apparatus for measuring concentration of a gaseious or particulate species using photoacoustic measurement of light adoption.

Background Information

Particulate matter (PM) refers to microscopic solid or liquid matter suspended in a gas, for example, air. One category of PM is atmospheric PM, (e.g., black carbon soot, atmospheric aerosol, and other species) that are produced as a byproduct of combustion, industrial processes or certain natural processes. Atmospheric PM can significantly impact human health. For example, atmospheric PM may be harmful if inhaled, leading to increase rates of lung cancer among other health problems. Likewise, atmospheric PM may absorb significant amounts of solar energy, promoting global climate change. For instance, black carbon soot is highly effective at absorbing solar energy, absorbing about a million times more energy per unit of mass than carbon dioxide ($CO_2$).

Another type of PM is commercial nanoparticles (e.g., ceramic silicon carbide nanoparticles, polymeric micelle nanoparticles, platinum-cobalt nanoparticles, and other species) that are synthesized for applications in manufacturing, biomedicine, optics, electronics and other fields. The properties of many conventional materials change when formed from very small particles, in part due to an increase in the ratio of surface area to weight that renders them more reactive. Such increase in reactivity has caused a growing interest in the production of commercially desirable PM species.

For both atmospheric and commercially produced PM there is often a need to measure the concentration of a PM species in a gas. One common measurement technique utilizes the photoacoustic (PA) effect. The PA effect is a process of acoustic wave generation from absorption of light. The basic theory behind the PA effect is that radiation energy from the light absorbed by a species of PM in a sample gas is released through non-radiative relaxation by generating heat in a localized region and creating an acoustic wave. Light absorption is normally proportional to the concentration of the species according to the Beer-Lambert law, which can be expressed as:

$$A = \sigma(\lambda) L c,$$

where A is a measure of absorbance, $\sigma(\lambda)$ is a wavelength-dependent absorptivity coefficient, L is the path length, and c is the concentration of the absorbing species. If $\tau(\lambda)$ and L are known, then by measuring absorbance, concentration of the species of PM may be determined.

A number of PA effect measurement instruments have been developed to attempt to measure concentration of species of PM in a sample gas. However, existing instruments generally suffer a number of shortcomings. First, existing instruments often experience high levels of interference from background absorption, background vibrations (i.e. background noise) and wall effects. Typically, such instruments employ a single sample cell in which the sample gas is subject to light, such that both the species of PM and gaseous species (e.g., nitrogen dioxide ($NO_2$)) in the sample contribute to the resulting acoustic wave. Further, background vibrations incident upon the sample cell from the surrounding environment are incorporated into the acoustic wave. Likewise, the effects of radiation energy on the walls of the sample cell further influence the acoustic wave.

Second, exiting instruments typically have lower than desired sensitivity, require significant volumes of sample gas, and have longer-than desired response times. A number of factors contribute to these issues, including the use a single microphone with limited sensitivity to detect the acoustic wave, and the use of a light source that has significant beam divergence requiring larger sized sample cells.

Third, existing instruments typically are sensitive to temperature, composition and humidity of the sample gas. Further, they often are sensitive to pressure change effects associated with flow of the sample gas. Such instruments often place their microphone in direct contact with the sample gas, resulting in interference and limiting response rate.

Accordingly, there is a need for improved apparatus and methods for measuring concentration of a species (e.g., a species of PM or, alternatively, a gas-phase species) using measurement of light absorption that may address some or all of these shortcomings.

SUMMARY

An improved photoacoustic effect measurement instrument and methods of configuration and operation thereof are provided for measuring a species (e.g., a species of PM or, alternatively, a gas-phase species) in a gas. The instrument may employ a pair of differential acoustic cells (including a sample cell for measurement of a sample gas including the species, and a reference cell for measurement of a filtered version of the sample gas from which the species has been substantially removed) to determine a differential signal. Use of a differential signal allows interference from background absorption, background vibrations and wall effects to be cancelled out. The instrument may also employ an array of multiple microphones with each acoustic cell, where the output signals of the microphones of the array are combined. Use of an array of multiple microphones allows for improved sensitivity. Still further, a thin film may be employed between the microphones and the interior of the acoustic cells to isolate the microphones from the sample gas therein. Isolating the microphones may reduce their sensitivity to temperature, composition and humidity of the sample gas, as well as pressure change effects associated with flow of the sample gas.

In one specific example embodiment, a photoacoustic effect measurement instrument for measuring a species (e.g., a species of PM such as black carbon soot) in a gas has a pair of differential acoustic cells, including a sample cell configured to receive sample gas including the species, and a reference cell configured to receive a filtered version of the sample gas from which the species has been substantially removed. Each of the acoustic cells includes an acoustic resonator and two acoustic attenuators. An excitation light source (e.g., a diode-pumped solid state (DPSS) laser) provides an amplitude modulated beam to each of the acoustic cells. The excitation light source is controlled by a waveform generated by a function generator. One or more microphones are mounted to each of the acoustic cells, and measure an acoustic wave generated in the respective acoustic cell by absorption of light therein, to produce a respective signal. The one or more microphones may be an array of multiple microphones (e.g., MicroElectrical-Mechanical System (MEMS) microphones mounted on a printed circuit boards (PCB)) whose output signals are combined to form the signal for the acoustic cell. The microphones may be disposed over an opening in the acoustic resonator of each of the acoustic cells. A thin film (e.g., an aluminized polyester film) may be used to isolate the microphones from the sample gas internal to each acoustic cell. A bandpass preamplifier tuned to the acoustic resonance frequency of the acoustic resonators determines a differential signal from the signals produced for each of the acoustic cells. The differential signal is provided to a lock-in amplifier along with the waveform from the function generator, which demodulates the waveform from the differential signal, to produce a demodulated differential signal. A controller calculates concentration of the species based on the demodulated differential signal, which may then be output (e.g., to a user interface or stored).

It should be understood that a variety of additional features and alternative embodiments may be implemented other than those discussed in this Summary. This Summary is intended simply as a brief introduction to the reader for the further description which follows, and does not indicate or imply that the examples mentioned herein cover all aspects of the disclosure, or are necessary or essential aspects of the disclosure.

BRIEF DESCRIPTION OF THE DRAWINGS

The description below refers to the accompanying drawings of example embodiments, of which.

DETAILED DESCRIPTION OF EXAMPLE EMBODIMENTS

Instrument Overview

Figure 1:
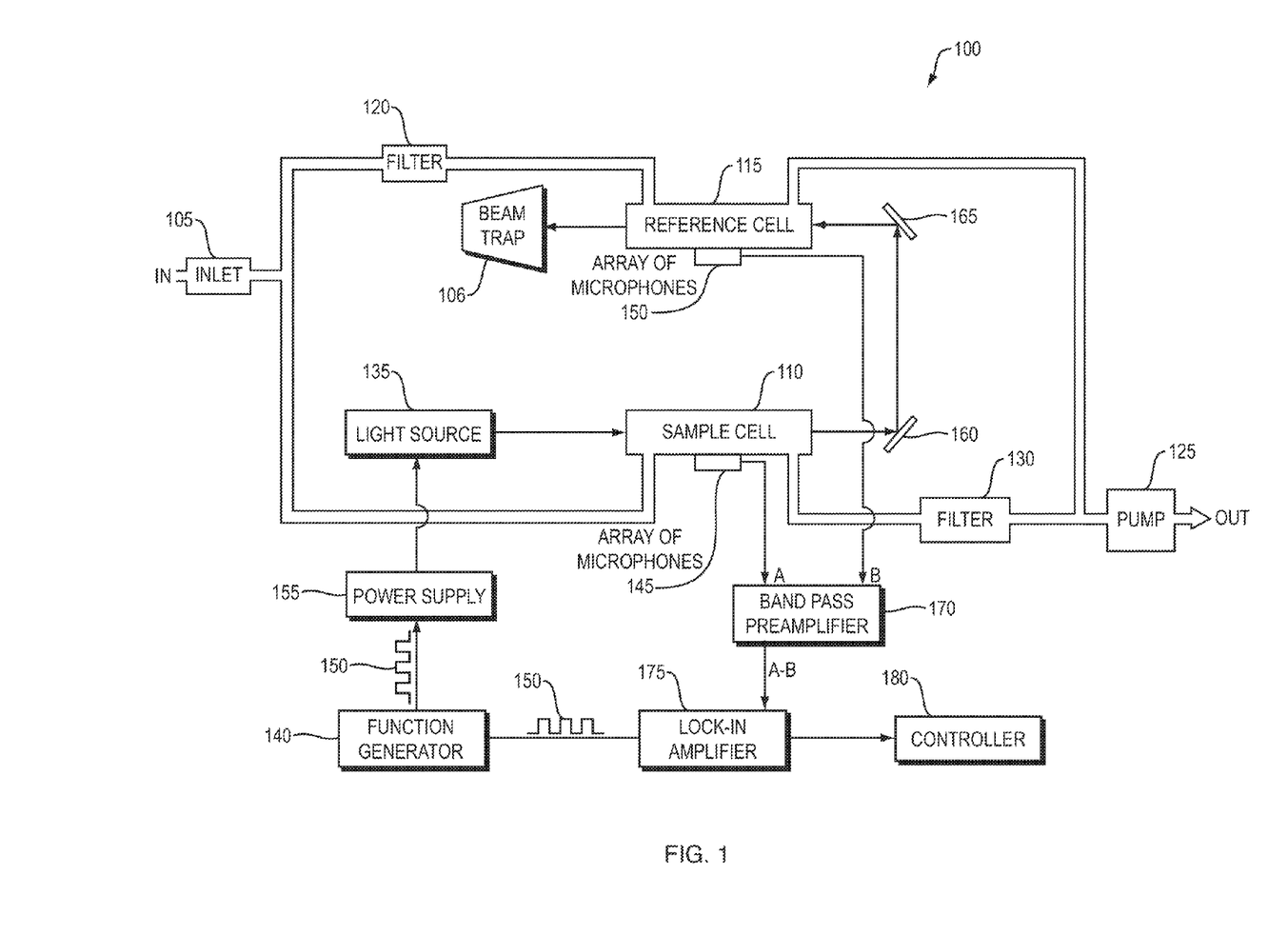
FIG. 1 is a block diagram of an example PA effect measurement instrument that may be used to measure concentration of a species in a gas.

FIG. 1 is a high level schematic block diagram of an example PA effect measurement instrument 100 that may be used to measure concentration of a species in a gas. In one example embodiment discussed in more detail below, the species is a species of PM, specifically black carbon soot. However, it should be understood that the PA effect measurement instrument 100 may be readily adapted to measure the concentration of a variety of other species, including other atmospheric PM and commercially produced PM, and gas-phase species.

The PA effect measurement instrument 100 includes an inlet 105 that receives a flow of sample gas including PM. The inlet 105 is coupled to differential acoustic cells, including a sample cell 110 and a reference cell 115. The sample gas including PM is provided directly to the sample cell 110, while a first filter 120 substantially removes PM from the sample gas provided to the reference cell 130. As used herein, "substantial removal" refers to the removal of at least 95% of a material. In one specific configuration, the first filter 120 removes 99.5% of PM.

The sample gas is evacuated from the sample cell 110 and the reference cell 115 after measurement by a pump 125. The reference cell 115 is directly coupled to the pump 125, while an intervening filter 130 is employed between the sample cell 110 and the pump 125.

To perform a measurement of a species of PM, an excitation light source 135 provides an amplitude modulated beam at the resonance frequency of the differential acoustic cells 110, 115. The modulation may be performed by a function generator 140 that produces a waveform (e.g., a square wave or sine-wave) 150 that controls a power supply 155 of the light source 135. The waveform may also be supplied to a lock-in amplifier 175.

Each acoustic cell 110, 115 includes an acoustic resonator and two acoustic attenuators. An array of multiple microphones 145, 150 is mounted over an opening in the center of the acoustic resonator of each acoustic cell 110, 115, such that each of the microphones are located near the peak of the acoustic mode. The microphones of each array 145, 150 may be isolated from gas internal to the acoustic resonator by a thin film (e.g., an aluminized polyester film) disposed over the opening.

The amplitude modulate beam from the light source 135 is directed into the sample cell 110 and an acoustic wave is generated from the absorption of light by the PM species and any other species (e.g., various gaseous species) that may be therein. The acoustic wave is measured by the microphones of the first microphone array 145, and their low-power output signals combined (e.g., additively) to form a first signal (referred to as "signal A"). The modulated beam is then directed by mirrors 160, 165 into the reference cell 115 and an acoustic wave is generated from the absorption of light by the other gaseous species that may be therein. The acoustic wave is measured by the microphones of the second microphone array 150, and their low-power output signals combined (e.g., additively) to form a second signal (referred to as "signal B"). A beam trap 166 is employed to sink the beam after it passes through the acoustic cells 110, 115.

Signal A produced by the first microphone array 145 and signal B produced by the second microphone array 150 are provided to a bandpass preamplifier 170 tuned to the acoustic resonance frequency of the acoustic resonators of the acoustic cells, which determines a differential signal therefrom (i.e. signal A -signal B). Assuming the filter 120 has removed substantially all the PM from the sample gas entering the reference cell 115, the differential signal is substantially purely due to absorption by PM.

The differential signal is provided to the lock-in amplifier 175 that also receives the waveform 150, which serves as a known carrier waveform. The lock-in amplifier 175 demodulates the carrier waveform from the differential signal. The demodulated differential signal is then provided to a controller 180 (e.g., a computer), which calculates concentration of the species of the PM based on the Beer-Lambert law and outputs (e.g., shows in a user interface on a display screen or stores in an electronic storage device) a concentration measurement of the species of PM.

Excitation Light Source

In one example embodiment, the light source 135 is a DPSS laser that offers very small beam divergence (e.g., beam diameter at aperture of <=2.4 mm and preferably <=1.2 mm). The very small beam divergence may permit the use of acoustic cells (e.g., sample cell 110 and reference cell 115) that have a small cross section, and thereby low sample volume. It has been found that the signal produced from an acoustic cell is linearly proportional to the intensity of the light source and the concentration of the species of PM, but inversely proportional to the cross section of the acoustic cell. For example, the PA effect inside an acoustic cell can be calculated as:

$$\Delta P \times V = nR\Delta T = I_0 c \sigma l$$

where $\Delta P$ is the pressure change, V is volume of the sample gas, n is number of moles of the sample gas, R is ideal gas constant, $\Delta T$ is the temperature change due to light absorption, $I_0$ is laser intensity, c is the concentration of the species of PM, $\sigma$ is absorption cross section, and l is length of the acoustic cell. Considering a cylindrical acoustic cell, the acoustic pressure change due to the heating effect from PM light absorption is given as:

$$\Delta P = \frac{I_0 c \sigma l}{V} = \frac{I_0 c \sigma}{\pi r^2}$$

As can be seen, if the cross section is reduced, as may be permitted by using a DPSS laser with small beam divergence, increased detection sensitivity can be achieved.

Further, in one example embodiment, the function generator 130 uses a quartz crystal oscillator and generates the waveform 150 as a square-wave or sine-wave transistor-transistor-logic (TTL) output. The function generator 130 may replace the mechanical chopper found in some traditional PA effect measurement instruments.

Differential Acoustic Cells

In one example embodiment, the differential acoustic cells (i.e. the sample cell 110 and the reference cell 115) are two identical units, having the same dimensions and material compositions. The units each contain acoustic resonators whose frequency response is the same as the modulation frequency of the light source 135, and a pair of acoustic attenuators. In one specific configuration, each acoustic resonator is a 10 cm long cylinder with an outside diameter (OD) of 9.5 mm and an inside diameter (ID) of 3 mm, made of 304 stainless steel, and each acoustic attenuator is a cylindrical ¼-wave (5 cm) acoustic attenuator with an OD of 76 mm and an inner diameter of 51 mm, made from 6061 aluminum alloy.

Use of differential acoustic cells permits interference from background absorption, background vibrations and wall effects to be cancelled out. For example, any other gaseous species (e.g., $NO_2$) that may be in the sample gas supplied to the sample cell 110 will pass through filter 120 and also be supplied to the reference cell 120, and thereby contribute to the acoustic wave in both acoustic cells 110, 115. When the difference is determined by the bandpass preamplifier 170 between the first microphone array 145 coupled to the sample cell 110, and the second microphone array 150 coupled to the reference cell 150, the contribution by background absorption will cancel. Likewise, provided the acoustic cells 110, 115 are located close to each other, any background vibrations from the surrounding environment will contribute to the acoustic wave in both acoustic cells 110, 115 substantially equally. Accordingly, when the difference is determined by the bandpass preamplifier 170, the contribution by background vibration will cancel. Similarly, provided the acoustic cells 110, 115 are identical, any contribution to the acoustic wave from wall effects will cancel when the difference is determined by the bandpass preamplifier 170.

Figure 2:
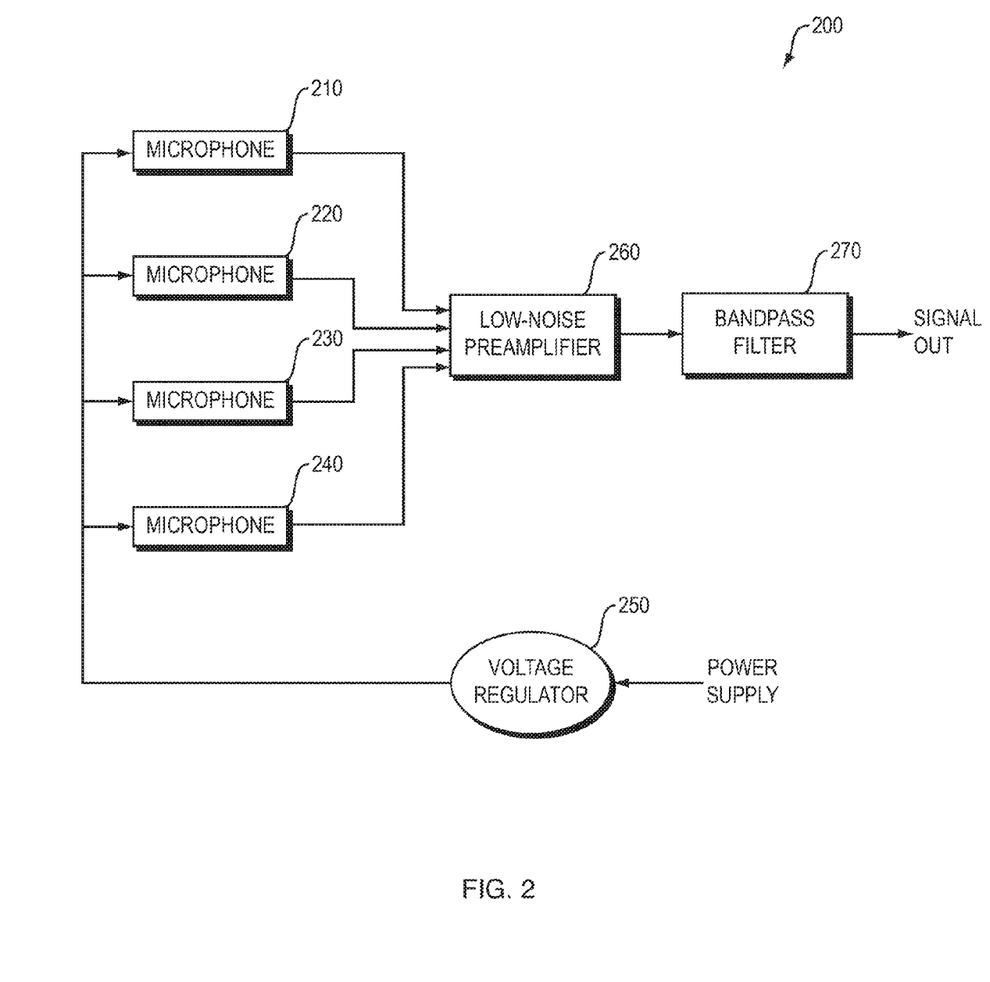
FIG. 2 is a schematic block diagram of an example microphone array PCB.

Further, in one example embodiment, the array of microphones 145, 150 used to detect the acoustic wave in each acoustic cell 110, 115 is an array of silicon membrane-based MEMS microphones mounted on a PCB, together with a low-noise preamplifier and a band pass filter. FIG. 2 is a schematic block diagram of an example microphone array PCB 200. In this example, the microphone array PCB includes 4 MEMS microphones 210-240, however it should be understood that a different number of microphones may be mounted on the PCB. The size of the MEMS microphones may be comparable to the ID of the acoustic resonator. In one specific configuration, each MEMS microphone may be approximately 3.8 mm in length and 2.7 mm in width. The MEMS microphones 210-240 may be powered via a voltage regulator 250 that provides a direct current (DC) output at a fixed voltage. Output from the MEMs microphones 210-240 may be supplied to a low-noise preamplifier 260 also mounted on the PCB 200, which combines the low-power signals from the microphones, and amplifies the combined signal several orders of magnitude. The amplified signal may then be supplied to a bandpass filter, which filters (e.g., in one specific configuration, with 40 decibel (db) noise reduction) frequencies other than the acoustic resonance frequency of the acoustic resonators.

Use of the array of microphones allows for improved sensitivity in comparison to signal microphone configurations. By combining the low-power signals from each of the microphones, the meaningful acoustic signal component outpaces acoustic noise. For example, the total signal may be represented as N×s, where N is the number of microphones and s is the acoustic signal from a signal microphone. Likewise, the total acoustic noise is proportional to the square-root of N. As a result, the signal-to-noise ratio of the combined signal may be improved by at least a factor of two for an example array of 4 microphones. Greater signal-to-noise ratio improvements may be achieved by further increasing the number of microphones.

Further, mounting the microphones on the same PCB offers additional advantages. Given the small size of the microphones, they would be difficult to directly mount on an acoustic cell. The PCB provides a convenient means for fixing the microphones at the center of the acoustic resonator of each acoustic cell. Further, mounting all the microphones together with the low-noise amplifier on the PCB reduces electronic noise that would occur from separation of these components.

Additionally, in one example embodiment, the microphones of each array 145, 150 are isolated from gas internal to the acoustic cell by a thin film that covers the opening in the acoustic resonator of the acoustic cell over which the microphones are mounted. In one specific configuration, the thin film is a 0.0005 mm thick aluminized polyester film interposed between the microphones and the sample gas. By isolating the microphones from the sample gas, impact on the detected acoustic waves from variations in temperature, composition and humidity of the sample gas is reduced. Further, the thin film prevents PM species in the sample gas in the sample cell 110 from accumulating inside of microphones, which could significantly deteriorate their performance over time. Further, isolating the microphones from the sample gas decreases interference in the acoustic measurement caused by pressure change effects associated with gas flow. In traditional configurations where a microphone is directly exposed to the sample gas, rapid gas flow inside the acoustic cell may cause strong interference in the acoustic measurement, effectively limiting the flow rate that may be employed, and therefore the response time of the instrument. Isolating the microphones from the sample gas with a thin film dramatically decrease their response to flow rate, permitting an increased flow rate to be used (e.g., 1 liter per minute), and thereby a more rapid response time to be achieved.

Phase Sensitive Data Processing

In one example embodiment, the bandpass preamplifier 170 that receives the signals from the first microphone array 145 and the second microphone array 150 is part of voltage measurement-enabled data acquisition device. The data acquisition device may receive the signals from the first microphone array 145 and the second microphone array 150 as analog voltage signals, and directly convert them into a differential digital signal. In one specific configuration, the data acquisition device has a dynamic range of ±10 volt (V) and 24-bit resolution, allowing for the recording of signals as low as 5 µV.

In one example embodiment, the lock-in amplifier 175 that receives the differential signal is configured to implement phase sensitive detection. In this phase sensitive detection, the waveform 150 is demodulated from the differential signal. In one specific configuration, the lock-in amplifier 175 is a lock-in amplifier module having a working frequency of 10 Hz to 45 KHz, where the working frequency is determined by an external signal input.

Methods of Configuration and Operation

Figure 3:
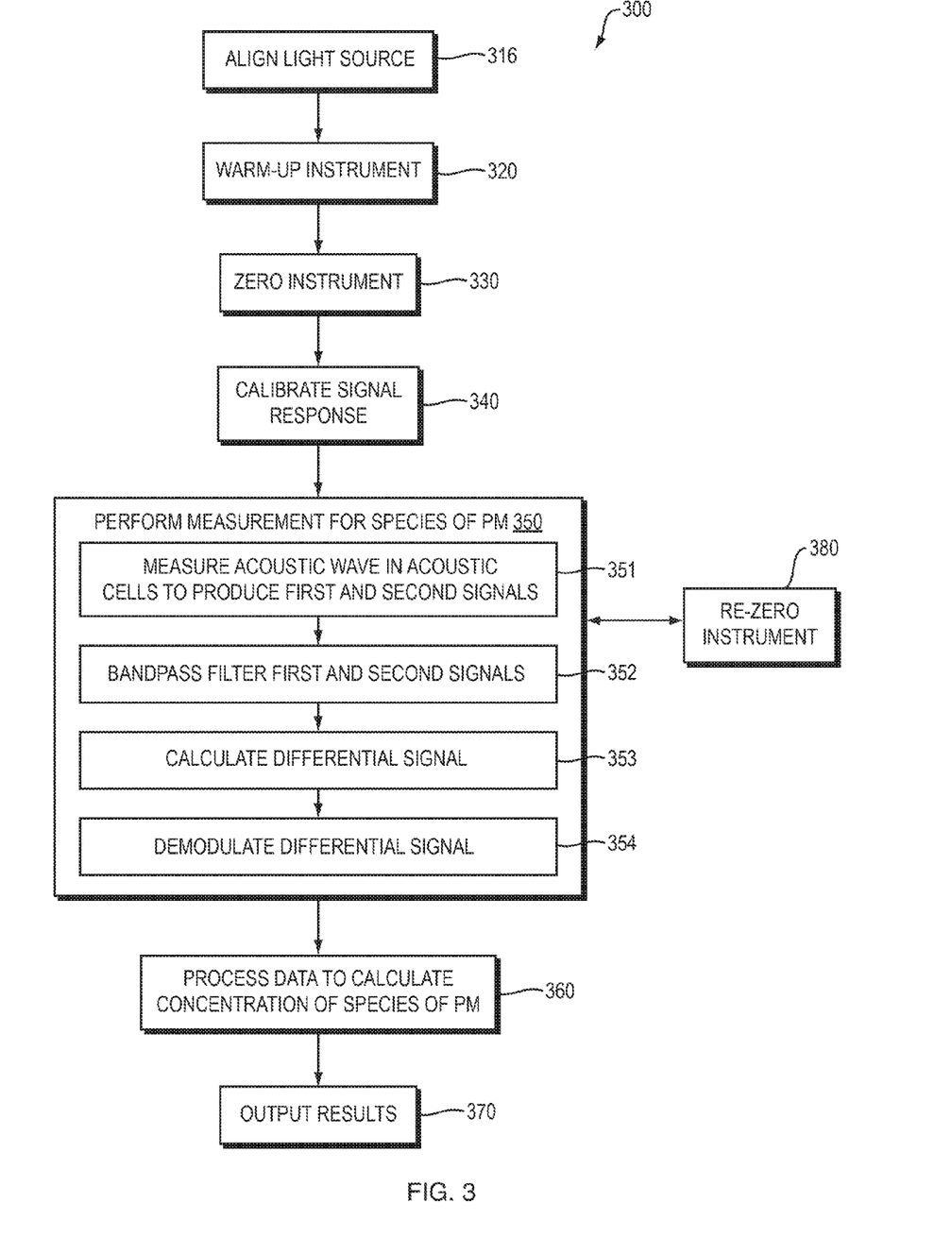
FIG. 3 is a flow diagram of an example sequence of steps for configuration and operation of the example PA effect measurement instrument of FIG. 1.

FIG. 3 is a flow diagram of an example sequence of steps 300 for configuration and operation of the example PA effect measurement instrument of FIG. 1. At step 310, the light source 135 (e.g., DPSS laser) and mirrors 160, 165 are aligned so that the beam passes through the acoustic resonators of the differential acoustic cells (i.e. the sample cell 110 and the reference cell 115). At step 320, the PA effect measurement instrument 100 is operated for a "warm up" period (e.g., 1 hour) to permit the light source 135 and arrays of microphones 145, 150 to achieve operational stability. At step 330, the instrument 100 is "zeroed". The zero point may be defined by the differential signal produced when sample gas with no PM is provided to the inlet 105, and a beam is passed into the acoustic cells 110, 115. At step 340, linearity of signal response is calibrated with specific concentrations of absorption standard in the sample gas supplied to the inlet 105. At step 350, the instrument performs a measurement for a species of PM.

As part of step 350, a number of sub-steps are performed. Delving into these in more detail, at sub-step 351, a measurement is performed of the acoustic wave generated in the acoustic cells 110, 115, to produce a first signal for the sample cell and a second signal for the reference cell. At sub-step 352, the first signal and the second signal are bandpass filtered to a resonance frequency of the acoustic resonators of the differential acoustic cells, and at sub-step 353, a differential signal is calculated from the first signal and the second signal. At sub-step 354, the differential signal is demodulated to remove the carrier waveform.

At step 360, resulting data (i.e. the demodulated differential signal) is processed by the controller to calculate concentration of the species of the PM based on the Beer-Lambert law. At step 370, results are output by being shown in a user interface on a display screen or stored in an electronic storage device. At step 380, which may be executed periodically in place of measurement step 350 (e.g., once every 30 minutes), the zero point of the instrument 100 is rechecked and the instrument is "re-zeroed" to account for any background changes.

Concluding Remarks

In summary, the above description details improved apparatus and methods for measuring concentration of a species (e.g., a species of PM) using the PA effect. It should be understood that various adaptations and modifications may be made to what is described above, to suit various requirements of the measurement task. For example, while it is discussed above that the acoustic wave may be measured by an array of multiple microphones, it should be understood that other types of detectors capable of measuring a pressure pulse may alternatively be used.

Further, different aspects of the apparatus, or various method steps, may be used in isolation or in various subcombinations with other apparatus or steps. For example, an array of multiple microphones (or detectors) may be used in an instrument that includes only a single acoustic cell. Likewise, a thin film (e.g., an aluminized polyester film) may be used in an instrument that includes only a single microphone (or detector). Further, many specific additions may be made to the techniques. For example, while it is described above that a single array of microphones (e.g., mounted to a PCB) may be used on each acoustic cell, it should be understood that, in alternative embodiments, multiple arrays of microphones (or detectors) (e.g., each mounted to a different PCB) may be used. The arrays may be arranged radially about the major axis of the acoustic resonator (e.g., cylindrical acoustic resonator) of each acoustic cell, such that all the devices may be fit in an area near the peak of the acoustic mode. A wide variety of other alternatives are also possible. In general, it should be understood that the above descriptions are meant to be taken only by way of example.

What is claimed is:

1. A photoacoustic effect measurement instrument for measuring a species in a gas, comprising:
    a pair of differential acoustic cells including
        a sample cell configured to receive sample gas including the species, and
        a reference cell configured to receive a filtered version of the sample gas from which the species has been substantially removed;
    an excitation light source configured to provide an amplitude modulated beam to each of the differential acoustic cells;
    one or more microphones mounted to each of the differential acoustic cells, and configured to measure an acoustic wave generated in the respective acoustic cell by absorption of light by sample gas therein and to produce a respective signal, the one or more microphones isolated from sample gas internal to the acoustic cells;
    a preamplifier configured to determine a differential signal from the signals produced for each of the differential acoustic cells; and
    a controller configured to calculate concentration of the species based on the differential signal.

2. The photoacoustic effect measurement instrument of claim 1, wherein the species is a species of particulate matter (PM).

3. The photoacoustic effect measurement instrument of claim 1, further comprising:
    a function generator configured to generate a waveform that controls the excitation light source; and
    a lock-in amplifier configured to receive the differential signal from the preamplifier and the waveform from the function generator, and to demodulate the waveform from the differential signal to produce a demodulated differential signal, wherein the controller is coupled to the lock-in amplifier and configured to calculate the concentration of the species based on the demodulated differential signal.

4. The photoacoustic effect measurement instrument of claim 1, wherein each of the differential acoustic cells includes an acoustic resonator and a pair of acoustic attenuators, and the preamplifier is a bandpass preamplifier that is tuned to an acoustic resonance frequency of the acoustic resonators of the differential acoustic cells.

5. The photoacoustic effect measurement instrument of claim 1, wherein the excitation light source is a diode-pumped solid state (DPSS) laser.

6. The photoacoustic effect measurement instrument of claim 1, wherein the one or more microphones mounted to each of the differential acoustic cell are an array of multiple microphones whose output signals are combined to form the signal for the differential acoustic cell.

7. The photoacoustic effect measurement instrument of claim 6, wherein the array of multiple microphones is an array of multiple membrane-based MicroElectrical-Mechanical System (MEMS) microphones mounted on a printed circuit boards (PCB).

8. The photoacoustic effect measurement instrument of claim 1, wherein the one or more microphones are mounted over an opening in each of the differential acoustic cells and are isolated from sample gas internal to the acoustic cell by a film disposed over the opening.

9. The photoacoustic effect measurement instrument of claim 1, wherein the film is an aluminized polyester film.

10. The photoacoustic effect measurement instrument of claim 1, wherein the species is black carbon soot.

11. A photoacoustic effect measurement instrument for measuring a species in a gas, comprising an acoustic cell configured to receive sample gas including the species;

an excitation light source configured to provide an amplitude modulated beam to the acoustic cell;

an array of multiple microphones mounted to the acoustic cell, each microphone configured to measure an acoustic wave generated in the acoustic cell by absorption of light by sample gas therein, wherein output signals from the multiple microphones of the array are combined to produce a combined signal; and a controller configured to calculate concentration of the species based on the combined signal.

12. The photoacoustic effect measurement instrument of claim 11, wherein the species is a species of particulate matter (PM).

13. The photoacoustic effect measurement instrument of claim 11, wherein the array of multiple microphones is an array of multiple membrane-based MicroElectrical-Mechanical System (MEMS) microphones mounted on a printed circuit boards (PCB).

14. The photoacoustic effect measurement instrument of claim 11, wherein the array of multiple microphones are mounted over an opening in the acoustic cell and are isolated from sample gas internal to the acoustic cell by a film disposed over the opening.

15. The photoacoustic effect measurement instrument of claim 11, further comprising:

a function generator configured to generate a waveform that controls the excitation light source; and a lock-in amplifier configured to receive the combined signal and to demodulate the waveform from the combined signal to produce a demodulated signal, and wherein the controller is coupled to the lock-in amplifier and configured to calculate the concentration of the species based on the demodulated signal.

16. The photoacoustic effect measurement instrument of claim 11, wherein the excitation light source is a diode-pumped solid state (DPSS) laser.

17. A photoacoustic effect measurement instrument for measuring a species in a gas, comprising an acoustic cell configured to receive sample gas including the species, the acoustic cell including an acoustic resonator having an opening;

a film mounted over the opening;

an excitation light source configured to provide an amplitude modulated beam to the acoustic cell;

one or more detectors mounted over the film and configured to measure an acoustic wave generated in the acoustic cell by absorption of light by sample gas therein and to produce a signal;

a controller configured to calculate concentration of the species based on the signal, wherein the film isolates the one or more detectors from the sample gas internal to the acoustic cell.

18. The photoacoustic effect measurement instrument of claim 17, wherein the species is a species of particulate matter (PM).

19. The photoacoustic effect measurement instrument of claim 17, wherein the one more detectors are one or more microphones.

20. The photoacoustic effect measurement instrument of claim 19, wherein the one or more microphones are an array of multiple microphones whose output signals are combined to form the signal for the acoustic cell.

21. The photoacoustic effect measurement instrument of claim 20, wherein the array of multiple microphones is an array of multiple membrane-based MicroElectrical-Mechanical System (MEMS) microphones mounted on a printed circuit boards (PCB).

22. The photoacoustic effect measurement instrument of claim 17, further comprising:

a function generator configured to generate a waveform that controls the excitation light source; and a lock-in amplifier configured to receive the combined signal and to demodulate the waveform from the combined signal to produce a demodulated signal, wherein the controller is coupled to the lock-in amplifier and configured to calculate the concentration of the species based on the demodulated signal.

23. The photoacoustic effect measurement instrument of claim 17, wherein the excitation light source is a diode-pumped solid state (DPSS) laser.

24. A method for photoacoustic measurement of a species in a gas, comprising:

measuring an acoustic wave generated in a pair of differential acoustic cells exposed to a beam from an excitation light source, the pair of differential acoustic cells including a sample cell containing sample gas including the species, and a reference cell containing a filtered version of the sample gas from which the species has been substantially removed, the measuring performed by one or more detectors isolated from sample gas internal to the acoustic cells that produce a first signal for the sample cell and a second signal for the reference cell;

determining a differential signal from the first signal and the second signal;

calculating a concentration of the species based on differential signal; and     outputting the concentration of the species.

25. The method of claim 24, where the species is a species of particulate matter (PM).

26. The method of claim 24, wherein the beam from the excitation light source is amplitude modulated based on a waveform, and the method further comprises:

demodulating the waveform from the differential signal to produce a demodulated differential signal, and     wherein the calculating calculates the concentration of the species based on the demodulated differential signal.

27. The method of claim 24, wherein each of the differential acoustic cells includes an acoustic resonator and a pair of acoustic attenuators, and the method further comprises:

bandpass filtering the first signal and the second signal to a resonance frequency of the acoustic resonators of the differential acoustic cells.

28. The method of claim 24, wherein the one or more detectors is an array of multiple microphones mounted to each of the differential acoustic cells, and the method further comprises:

combining output signals from the microphones of each array of multiple microphones to produce the first signal and the second signal, respectively.

29. The method of claim 28, wherein each array of multiple microphones is an array of multiple membrane-based MicroElectrical-Mechanical System (MEMS) microphones mounted on a printed circuit boards (PCB).

30. The method of claim 24, wherein the one or more detectors are mounted over an opening in each of the differential acoustic cells, and the one or more detectors are isolated from sample gas internal to the acoustic cell by a film disposed over the opening.

\* \* \* \* \*